United States Patent
Li et al.

(10) Patent No.: US 11,202,577 B2
(45) Date of Patent: Dec. 21, 2021

(54) SYSTEM FOR MONITORING CARDIOVASCULAR AND BRAIN FUNCTION IN COMBINATION WITH PHYSIOLOGICAL DETECTION DEVICE AND METHOD THEREOF

(71) Applicants: Ming-Hsin Li, Taoyuan (TW); Kai-Hung Cheng, Taoyuan (TW); Shih-Wei Lo, Taoyuan (TW)

(72) Inventors: Ming-Hsin Li, Taoyuan (TW); Kai-Hung Cheng, Taoyuan (TW); Shih-Wei Lo, Taoyuan (TW)

(73) Assignee: INSTITUTE of NUCLEAR ENERGY RESEARCH, ATOMIC ENERGY COUNCIL, EXECUTIVE YUAN

( * ) Notice: Subject to any disclaimer, the term of this patent is extended or adjusted under 35 U.S.C. 154(b) by 133 days.

(21) Appl. No.: 16/664,946

(22) Filed: Oct. 28, 2019

(65) Prior Publication Data

US 2021/0121074 A1 Apr. 29, 2021

(51) Int. Cl.
| | | |
|---|---|---|
| *A61B 5/0205* | (2006.01) | |
| *A61B 5/029* | (2006.01) | |
| *A61B 5/00* | (2006.01) | |
| *A61B 5/021* | (2006.01) | |

(Continued)

(52) U.S. Cl.
CPC .......... *A61B 5/0205* (2013.01); *A61B 5/0002* (2013.01); *A61B 5/029* (2013.01); *A61B 5/369* (2021.01); *A61B 5/4076* (2013.01); *A61B 5/6803* (2013.01); *A61B 5/7275* (2013.01); *A61B 5/024* (2013.01); *A61B 5/02108* (2013.01); *A61B 5/02438* (2013.01)

(58) Field of Classification Search
CPC ..... A61B 5/0205; A61B 5/369; A61B 5/4076; A61B 5/6803; A61B 5/029; A61B 5/7275; A61B 5/0002; A61B 5/02108; A61B 5/024

See application file for complete search history.

(56) References Cited

U.S. PATENT DOCUMENTS

| | | | |
|---|---|---|---|
| 2016/0073990 A1* | 3/2016 | Nakajima | A61B 6/4258 600/431 |
| 2016/0287166 A1* | 10/2016 | Tran | A61B 5/165 |
| 2018/0132794 A1* | 5/2018 | Lange | A61B 5/4035 |

(Continued)

OTHER PUBLICATIONS

Yoshita et al. "Diagnostic Accuracy of 123I-Metalodobenzylguanidine Myocardial Scintigraphy in Dementia with Lewy Bodies: A Multicenter Study" Mar. 20, 2015; PLOS ONE, pp. 1-13 (Year: 2015).*

(Continued)

*Primary Examiner* — Brian T Gedeon
*Assistant Examiner* — Joshua Andrew Schum-Houck

(57) ABSTRACT

A system and method for monitoring cardiovascular and brain functions in combination with a physiological detection device, which uses a smart wearable device to detect physiological data such as heart rate and pulse pressure of a user, and transmits the physiological data to an arithmetic function. An electronic device in which a preset function and a calculation formula are built in, and the physiological data can be converted into corresponding determination parameters to monitor the possibility and risk of cardiovascular diseases and neurodegenerative diseases.

9 Claims, 16 Drawing Sheets

(51) Int. Cl.
*A61B 5/024* (2006.01)
*A61B 5/369* (2021.01)

(56) References Cited

U.S. PATENT DOCUMENTS

2018/0147304 A1* 5/2018 Provost .................. G01N 33/60
2018/0166174 A1* 6/2018 Lewis ..................... G16H 50/20
2018/0325407 A1* 11/2018 Varadan ............. A61B 5/02108

OTHER PUBLICATIONS

Arimoto et al. "Dynamic 123I-MIBG SPECT reflects sympathetic nervous integrity and predicts clinical outcome in patients with chronic heart failure" 2004; Annals of Nuclear Medicine vol. 18, No. 2, 145-150 (Year: 2004).*

Spinelli et al. "Relationship between left ventricular diastolic function and myocardial sympathetic denervation measured by 123I-meta-iodobenzylguanidine imaging in Anderson-Fabry disease" Eur J Nucl Med Mol Imaging (2016) 43:729-739 (Year: 2016).*

Shinichiro et al. "Assessment of myocardial washout of Tc-99m-sestamibi in patients with chronic heart failure: Comparison with normal control" Annals of Nuclear Medicine vol. 16, No. 4, 237-242, 2002 (Year: 2002).*

Nakajima et al. "Creation of mortality risk charts using 123Imeta-iodobenzylguanidine heart-to-mediastinum ratio in patients with heart failure: 2- and 5-year risk models" European Heart Journal—Cardiovascular Imaging (2016) 17, 1138-1145 (Year: 2016).*

* cited by examiner

| Delayed H/M ratio | Heart disease risk | Consequence |
|---|---|---|
| <1.1 | risk of cardiac mortality is >20% within two years. | high risk, an immediate hospital examination is recommended. |
| <1.6 | 1. risk of heart disease death about 6.7%, and probability of death is nearly 10.1%.<br>2. it has related events previously, and the possibility of heart failure or arrhythmia or heart attack is 37% within two years. | medium risk, a hospital detailed examination is recommended. |
| ≥1.6 | 1. risk of heart disease death about 1.0%, and probability of death is nearly 2%.<br>2. it has related events previously, and the possibility of heart failure or arrhythmia or heart attack is 15% within two years. | medium risk, a hospital examination is recommended. |
| ≥1.8 | risk of cardiac mortality is nearly 0% within two years | low risk to be monitored periodically |

Fig. 9

| Delayed H/M ratio | Risk of neurodegenerative disease | Consequence |
| --- | --- | --- |
| >2.4 | nil | low risk to be monitored periodically |
| 1.8-2.4 | risk of first stage Parkinson's disease and multiple system atrophy | medium risk, a hospital examination is recommended. |
| 1.4-1.8 | risk of developing Parkinson's disease in the first and/or second stage and progressive supranuclear palsy | medium risk, an immediate hospital examination is recommended. |
| 1.3-1.4 | risk of second to third stage Parkinson's disease | medium to high risk, an immediate hospital detailed examination is recommended. |
| <1.3 | risk of third to fifth stage Parkinson's disease, Alzheimer's disease and dementia with Lewy bodies | high risk, an immediate hospital detailed examination is recommended. |

Fig. 11

SYSTEM FOR MONITORING CARDIOVASCULAR AND BRAIN FUNCTION IN COMBINATION WITH PHYSIOLOGICAL DETECTION DEVICE AND METHOD THEREOF

BACKGROUND OF THE INVENTION

1. Field of the Invention

The invention relates to a system and a method for monitoring cardiovascular and brain functions in combination with a physiological detection device, in particular to automatically monitoring personal physiological data by using a smart wearing device, and converting the physiological data into a determination through a preset function and a program to monitor the trend of a user suffering from cardiovascular and neurodegenerative diseases.

2. Description of Related Art

The current common cardiovascular examinations include: blood drawing, electrocardiogram, ultrasound, nuclear medicine myocardial perfusion, computed tomography and cardiac catheterization, in which blood draw mainly measures blood sugar and cholesterol; cardiac ultrasound mainly observes the structure of the heart and the state of motion, but because the coronary arteries are subtle, it is sometimes difficult to accurately determine whether there is a blockage; although 90% in accuracy of myocardial perfusion in nuclear medicine is higher than about 70% in accuracy of exercise electrocardiogram, there is a problem of radioactivity and long inspection time; the two-step examination of computed tomography and cardiac catheterization is due to implication of health insurance and invasive examination only used after diagnosis of the disease.

Nuclear medicine angiography is currently widely used for the diagnosis of cardiovascular disease to monitor the prognosis of sudden cardiac death and heart failure. Clinical studies have also found that nuclear medicine cardiac angiography can also be used to assess the distribution and function of sympathetic nerves that distinguishes some of the neurodegenerative diseases, including Parkinson's disease and Louis's dementia. In addition, it is observed that the heart rate, heart pressure, and heart/mediastinum count ratio (H/M) in clinical data of clinical patients may reveal a certain degree of relevance. The heart/mediastinum count ratio calculated from the above physiological data connected to the nuclear CT image can be used to monitor sudden death from heart failure, prognosis assessment of heart failure, Parkinson's disease and dementia.

Like nuclear medicine myocardial perfusion, nuclear medicine cardiac angiography also has problems with long-term radioactivity and long-term examination. Although cardiac angiography results can be used for cardiovascular disease diagnosis, prognosis assessment, and differentiation of some neurodegenerative diseases. To achieve the purpose abovementioned, the quantification and standardization of image data is very important. In foreign countries, image data quantification and standardization between different devices have been successfully established. However, the result of the quantification of quantitative data at the source of nuclear medicine imaging may still be affected by different personnel who in charge of the image interpretation, and it takes more time to quantize image data with labor work. However, with the advancement of technology and the booming of wearable devices, heart rate, ECG, blood pressure and blood pressure, and physiological data such as blood oxygen can be monitored at any time through smart wearable devices such as apple watch, Xiaomi bracelet, ASUS VivoWatch BP, JSmax sports bracelet. Therefore, human body big data collection is much easier than before, and in combination with the advancement of artificial intelligence technology, as long as a more accurate model is established through a large amount of physiological data combined with image data calculation, the physiological data collected by the wearable device, and the risk of heart and neurodegenerative diseases can be accurately monitored in the near future.

In the U.S. Pat. No. 7,413,546 B2 patent, a technique for collecting and calculating cardiovascular data and calculating for diagnosis and monitoring of physical health is disclosed, and in the US 20170172423 A1 patent, a technique for detecting a neck sensor of physiological data is disclosed. However, the physiological data obtained in the cited prior arts is not linked to nuclear medicine imaging and disease diagnosis.

To overcome the shortcomings, the present invention tends to provide an improved systematic method for monitoring cardiovascular and brain function to mitigate and obviate the aforementioned drawbacks.

SUMMARY OF THE INVENTION

The main object of the present invention is to provide a physiological detection system for monitoring cardiovascular and brain functions in combination with a physiological detection device, which uses a wearable physiological detection device to detect an individual's physiological data and transmit the physiological data to an electronic device with arithmetic function. The physiological detection system of the present invention has a preset function and a calculation formula, which can convert the physiological data into measurement parameters, thereby monitoring the possibility and risk of cardiovascular diseases and neurodegenerative diseases. In comparison with the traditional professional testing instruments and analysis methods, the physiological detection device for monitoring cardiovascular and brain functions of the present invention provides an alternative with high accuracy at lower cost.

Another object of the present invention is to provide a physiological detection system for monitoring cardiovascular and brain functions in combination with a physiological detection device, which can completely avoid the damage of radioactive substances to the body during the detection process, and does not require professional image interpretation knowledge. Not only is it extremely safe and easy to use, but its accumulation of big data in the future can increase the accuracy of the research and will replace some of the current physiological examination items.

Another object of the present invention is to provide a physiological detection system for monitoring cardiovascular and brain functions in combination with a physiological detection device, which mainly collects physiological data such as a heart rate and a pulse pressure of a user, and the function relationship is set to the value of the washout ratio, and converted into the heart rate index value by a preset function relationship.

Converting the heart rate index value to an early or delayed heart/mediastinum count ratio by a predetermined functional relationship, and monitoring the early or delayed heart/mediastinum count ratio to the heart disease monitoring chart to monitor the risk of heart disease.

By indexing the early or delayed heart/mediastinum count ratio into a neurodegenerative disease surveillance chart to monitor whether a neurodegenerative disease exists.

Other objects, advantages and novel features of the invention will become more apparent from the following detailed description when taken in conjunction with the accompanying drawings.

BRIEF DESCRIPTION OF THE DRAWINGS

FIG. 9 is a diagram of the heart disease monitoring chart of the present invention (1).

FIG. 11 is a monitoring chart of the neurodegenerative disease of the present invention.

DETAILED DESCRIPTION OF THE PREFERRED EMBODIMENTS

Figure 1:
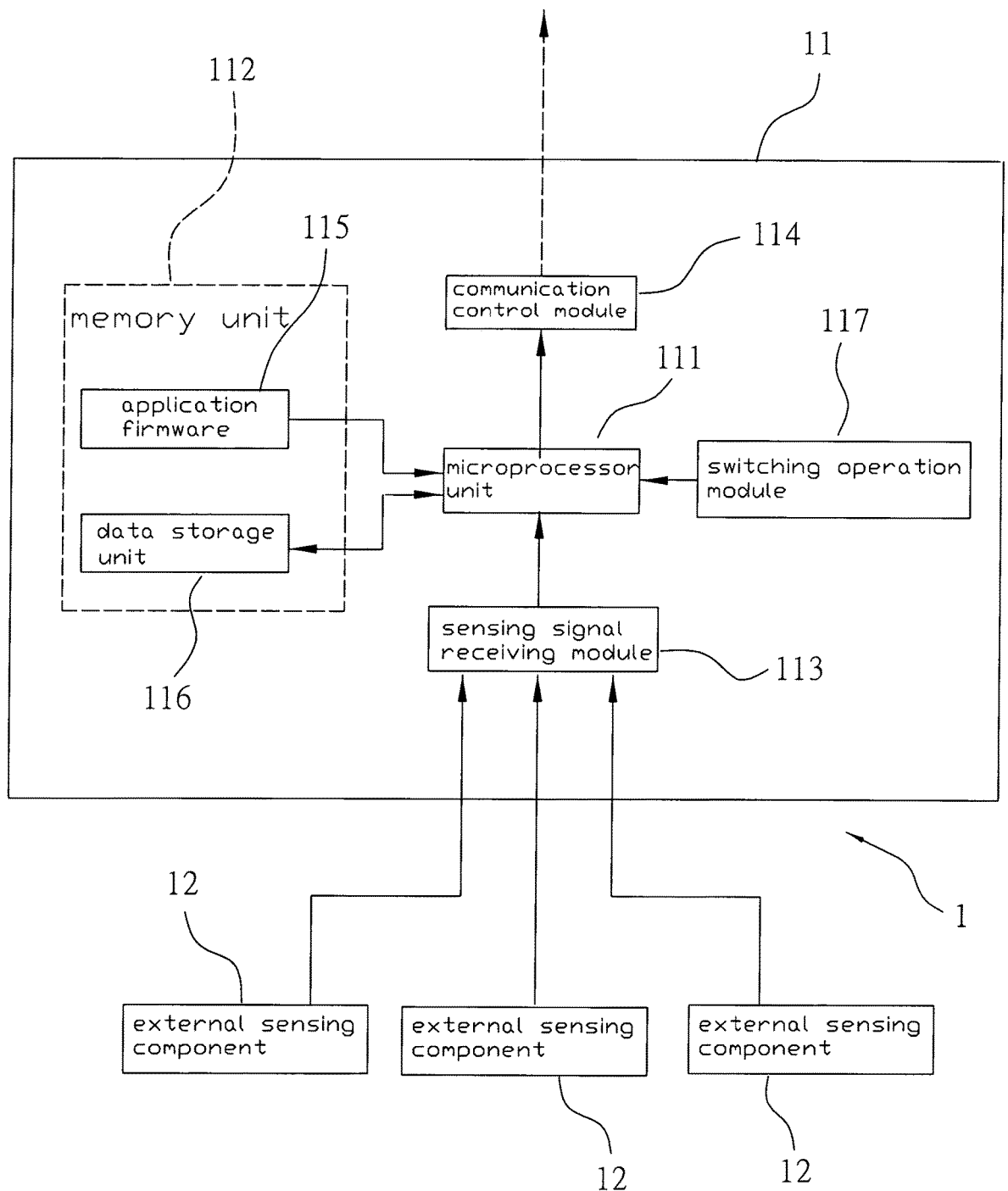
FIG. 1 is a block diagram showing a structure of a wearable physiological detecting device of the present invention.
Figure 2:
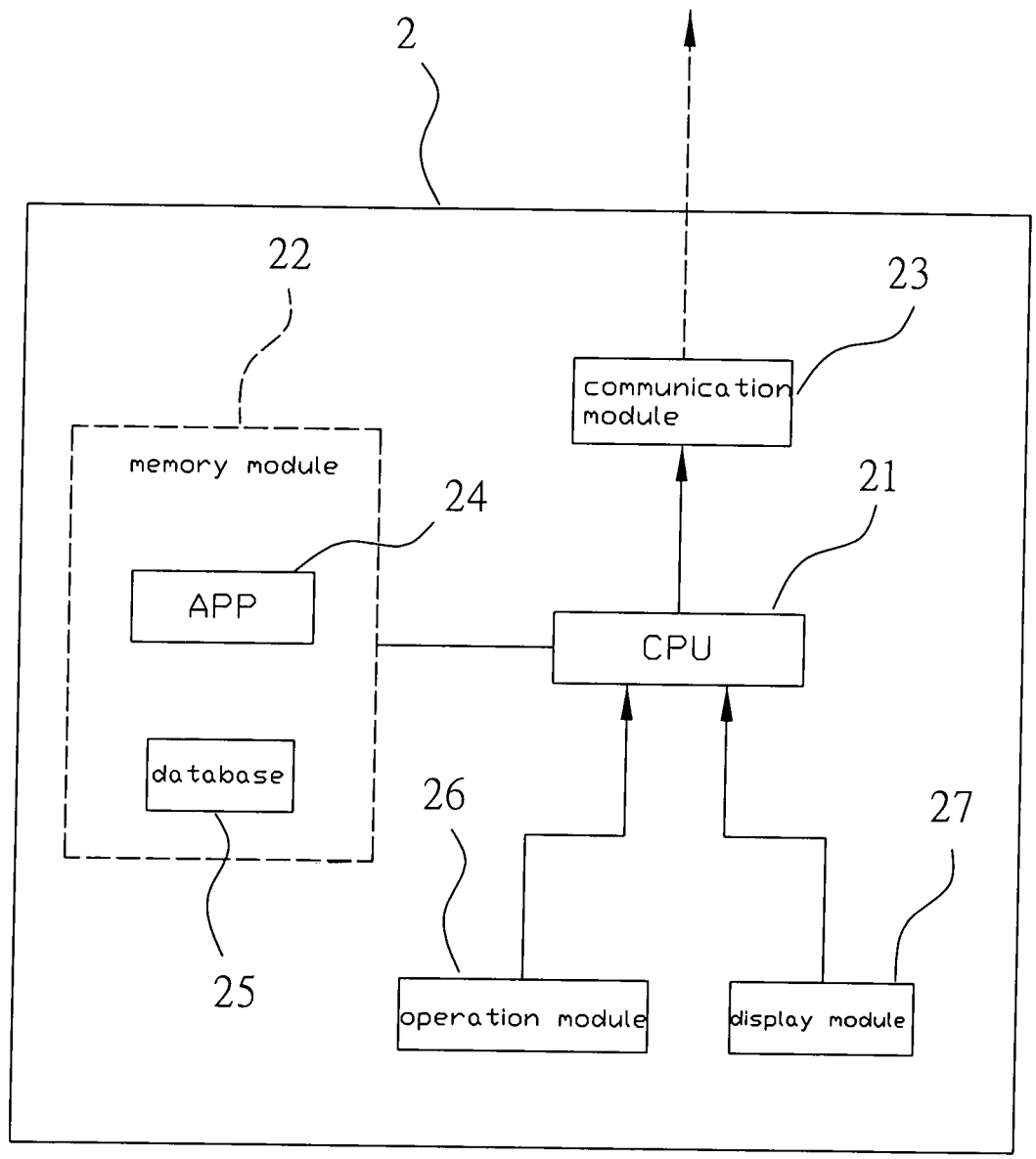
FIG. 2 is a block diagram showing the structure of the electronic device of the present invention.

As shown in the FIG. 1 and FIG. 2, the main structure of the present invention includes: a wearable physiological detecting device 1 and an electronic device 2; wherein the wearable physiological detecting device 1 has a host 11 and a plurality of external sensing elements 12, the host 11 is internally provided with a micro processing unit 111, a memory unit 112, a sensing signal receiving module 113, a communication control module 114, and a switching operation module 117. The external sensing component 12 is worn on a part of the human body where the head, neck, wrist, arm, foot or other human artery flows, and is detected by optical sensing, electrical signal measurement or pressure sensing. A corresponding sensing signal is generated for a physiological state, and the sensing signal is received by the sensing signal receiving module 113 and converted into various physiological data, and then transmitted to the micro processing unit 111. In addition, an application firmware 115 required for the overall operation of the wearable physiological detection device 1 is built-in the memory unit 112, which is further provided with a data storage unit 116 capable of storing the physiological data, and the micro processing unit 111 executes the application firmware 115 to control the communication control module 114 to transmit the physiological data to the paired external electronic device 2.

The electronic device 2 can be a personal computer, a notebook computer, a tablet computer, a mobile phone or other computing device, and has a central processing unit 21, a memory module 22, a communication module 23, an operation module 26 and a display module 27, and the communication module 23 can be paired with the communication control module 114 via a wired or wireless manner for receiving the physiological data and transmitting to the central processing unit 21. In addition to storing an application (APP) 24, the memory module 22 is provided with a database 25 for storing various data, and the application 24 has various calculation derivation functions, and the operation module 26 is to execute various control actions with the central processing unit 21; the display module 27 is to display each operation process and calculation analysis result. After the central processing unit 21 executes the application 24, the physiological data can be calculated and derived via each of the functional formulas to generate a monitoring analysis for the cardiovascular and brain function examination.

Referring to FIG. 3 through FIG. 7, it can be seen that the application 24 of the present invention has the following 5 categories functional formulas: Formula 1. Washout ratio and pulse pressure relationship function:

$$y=-0.6094x+63.325; R^2=0.3284; \rho<0.05$$

wherein y: washout ratio (WR); x:pulse pressure (PP); R2:coefficient of determination, when $R^2$ is closer to 1, the ability to interpret y with x is stronger; $\rho$: statistical difference value; if $\rho<0.05$), means that there is a significant difference; if $\rho<0.01$ means that there is a very significant difference; if $\rho<0.001$ means that there is a outstanding significant difference.

Formula 2. Washout ratio and heart rate relationship function:

$$y=0.2459x+12.111; R^2=0.4008; \rho<0.01$$

wherein y:washout ratio (WR); x:heart rate (HR); $R^2$:coefficient of determination, if $R^2$ is closer to 1, the ability to interpret y with x is stronger; $\rho$: statistical difference value; if $\rho<0.05$, means that there is a significant difference; if $\rho<0.01$ means that there is a very significant difference; if $\rho<0.001$ means there is a outstanding significant difference.

Formula 3. Washout ratio and strokestroke volume index function:

$$y=-0.7978x+70.826; R^2=0.3578; \rho<0.05$$

wherein y: stroke volume index (SVI); x: washout ratio (WR); $R^2$: coefficient of determination, if $R^2$ is closer to 1, the ability to interpret y with x is stronger; ρ: statistical difference value; if ρ<0.05, means that there is a significant difference; if ρ<0.01 means that there is a very significant difference; if ρ<0.001 means there is a outstanding significant difference.

Formula 4. Early heart/mediastinum ratio and stroke volume index function:

$$y=0.0162x+1.3379; R^2=0.4412; \rho<0.01$$

wherein y: early heart/mediastinum ratio (early H/M); x: stroke volume index (SVI); $R^2$: coefficient of determination, if $R^2$ is closer to 1, the ability to interpret y with x is stronger; ρ: statistical difference value; if ρ<0.05, means that there is a significant difference; if ρ<0.01 means that there is a very significant difference; if ρ<0.001 means there is a outstanding significant difference.

Formula 5. Delayed heart/mediastinum ratio and stroke volume index function:

$$y=0.0161x+1.0938; R^2=0.3897; \rho<0.01$$

wherein y: delayed heart/mediastinum ratio (delayed H/M); x: stroke volume index (SVI); $R^2$: coefficient of determination, if $R^2$ is closer to 1, the ability to interpret y with x is stronger; ρ: statistical difference value; if ρ<0.05, means that there is a significant difference; if ρ<0.01 means that there is a very significant difference; if ρ<0.001 means there is a outstanding significant difference.

Figure 3:
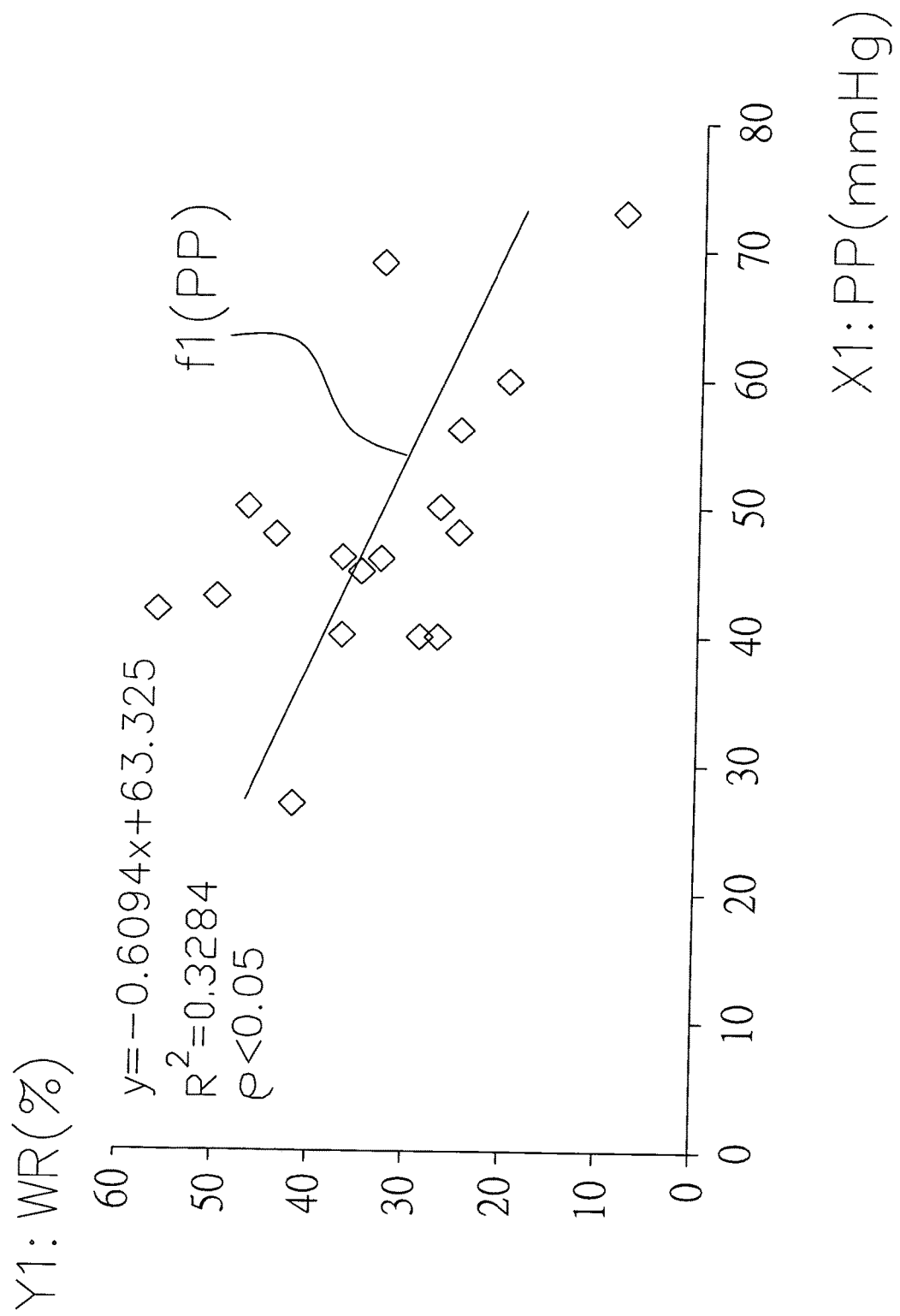
FIG. 3 is a graph showing the relationship between the washout ratio and pulse pressure of the present invention.
Figure 4:
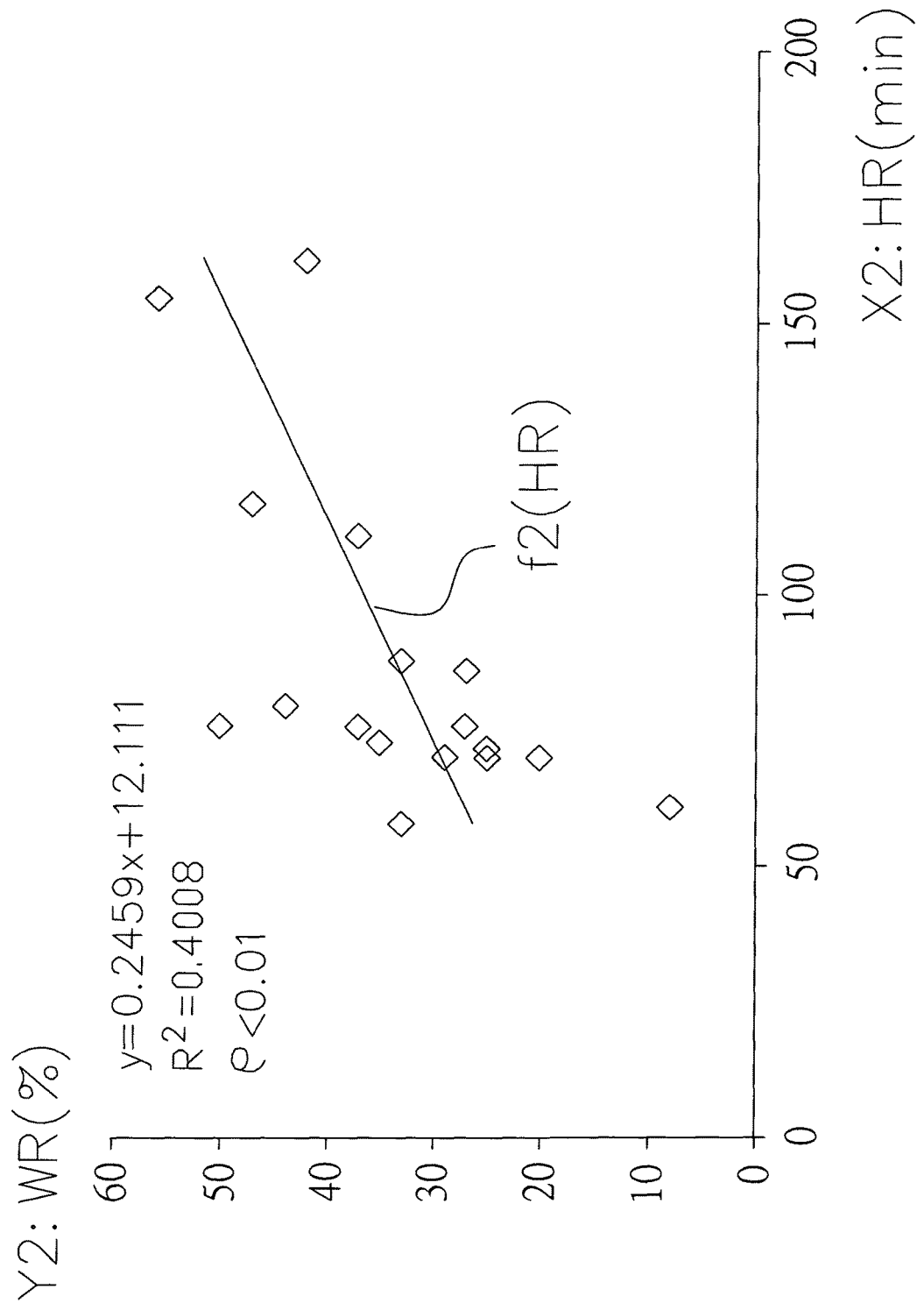
FIG. 4 is a graph showing the relationship between the washout ratio and the heart rate of the present invention.
Figure 5:
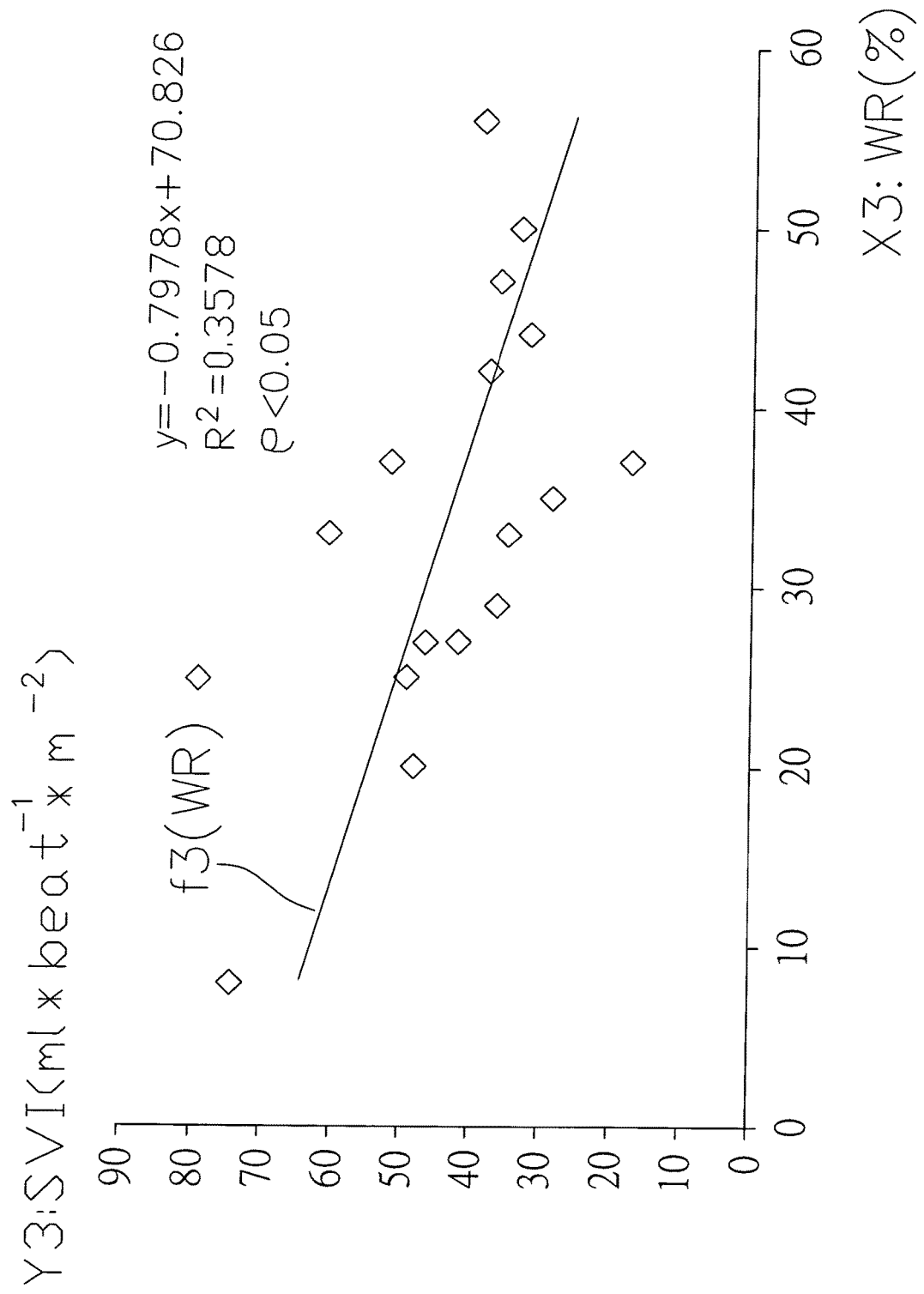
FIG. 5 is a graph showing the relationship between the washout ratio and the stroke volume index of the present invention.
Figure 6:
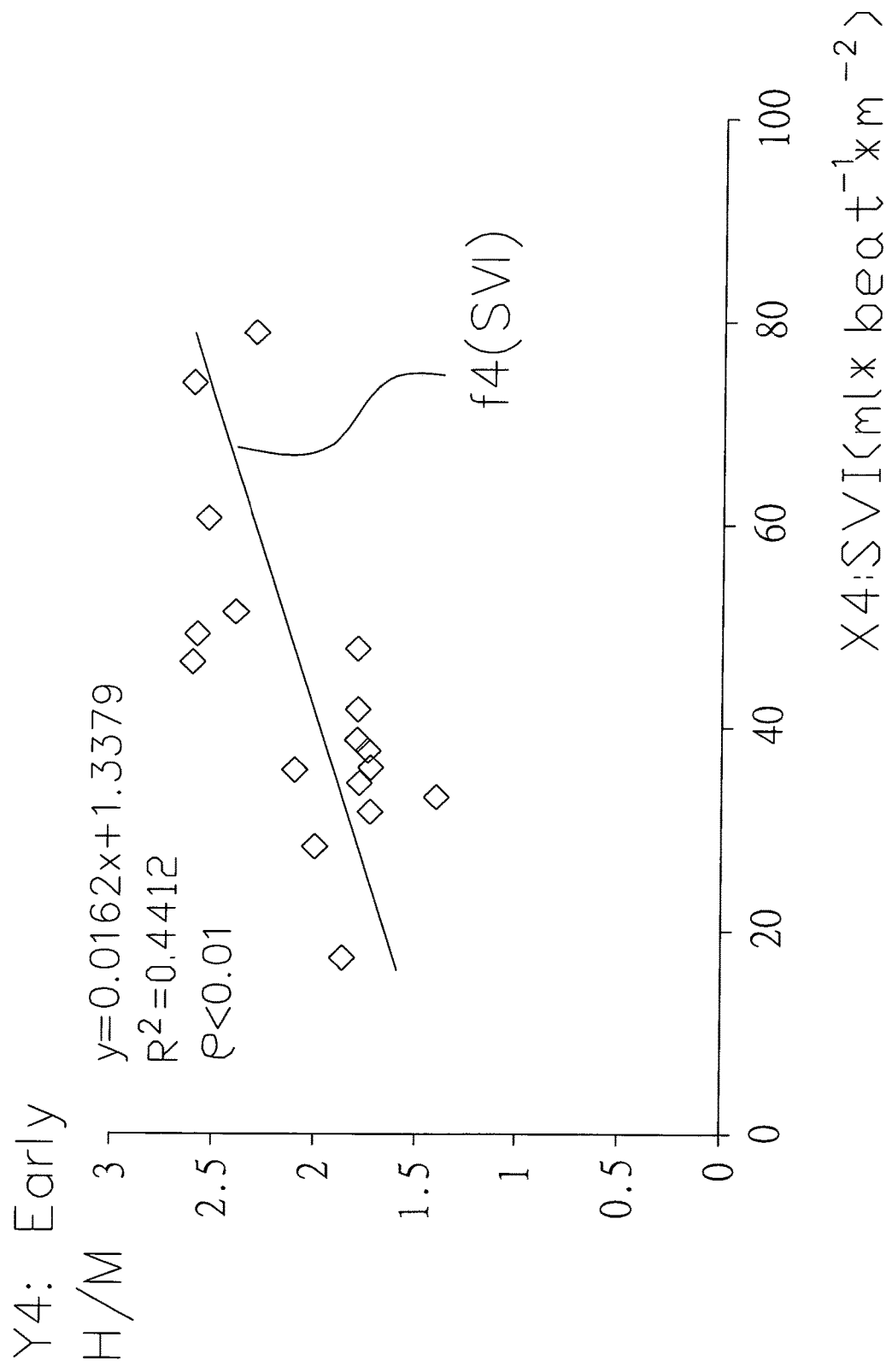
FIG. 6 is a graph showing the relationship between the early heart/mediastinum count ratio and the stroke volume index of the present invention.
Figure 7:
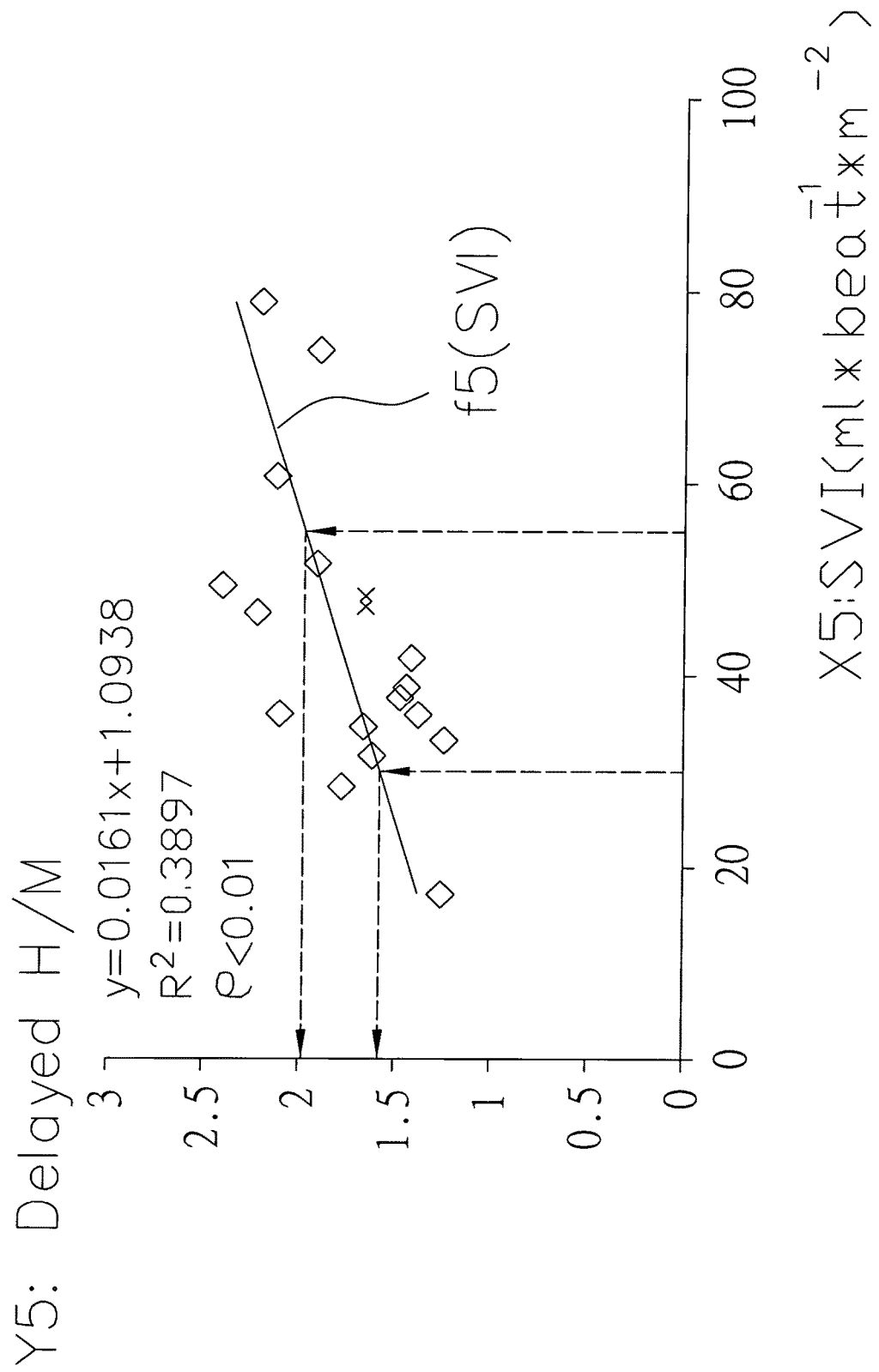
FIG. 7 is a graph showing the relationship between the delayed heart/mediastinum count ratio and the stroke volume index of the present invention.
Figure 8:
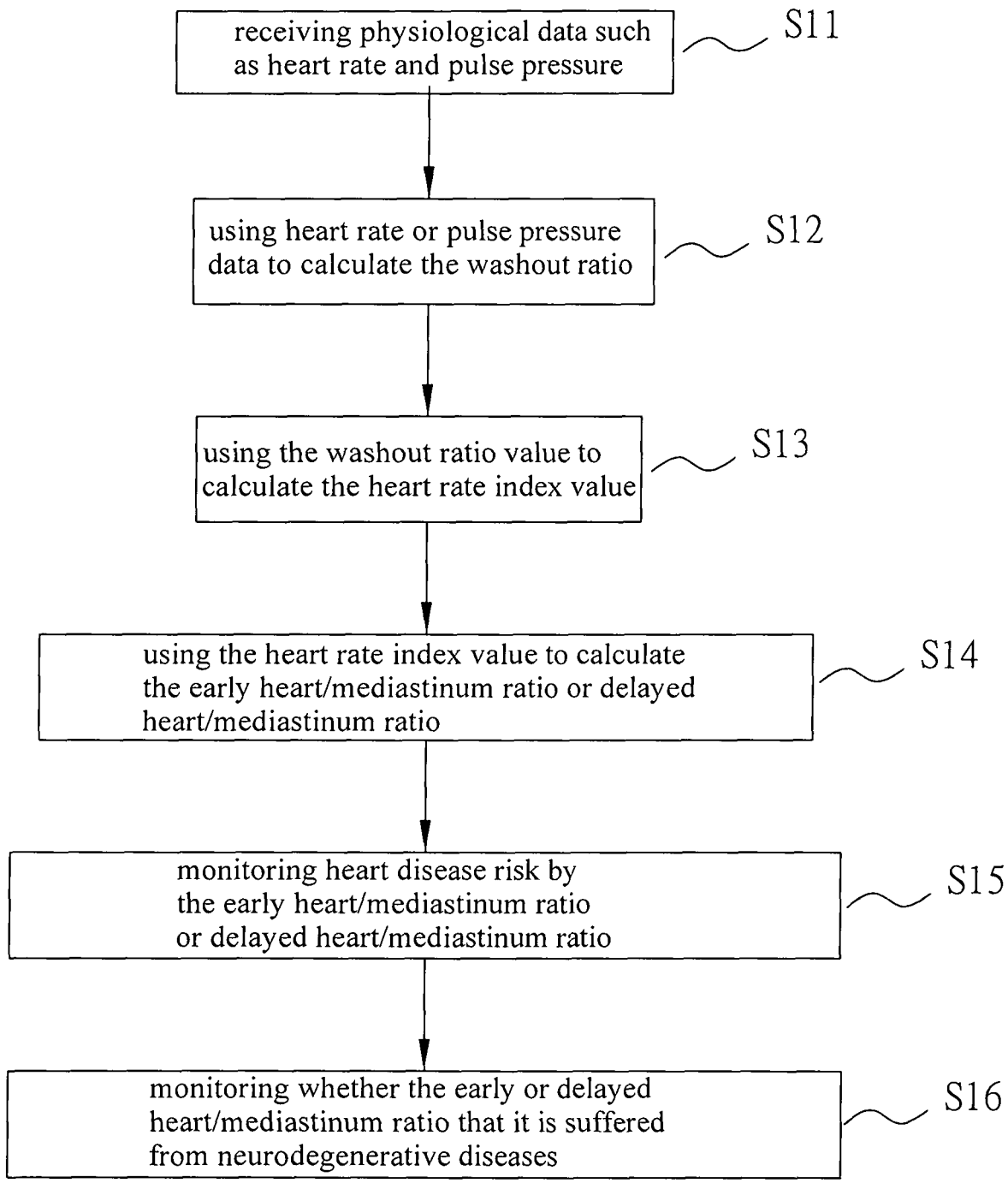
FIG. 8 is a flow diagram of a method of performing electronic and brain function monitoring by an electronic device of the present invention.
Figure 10:
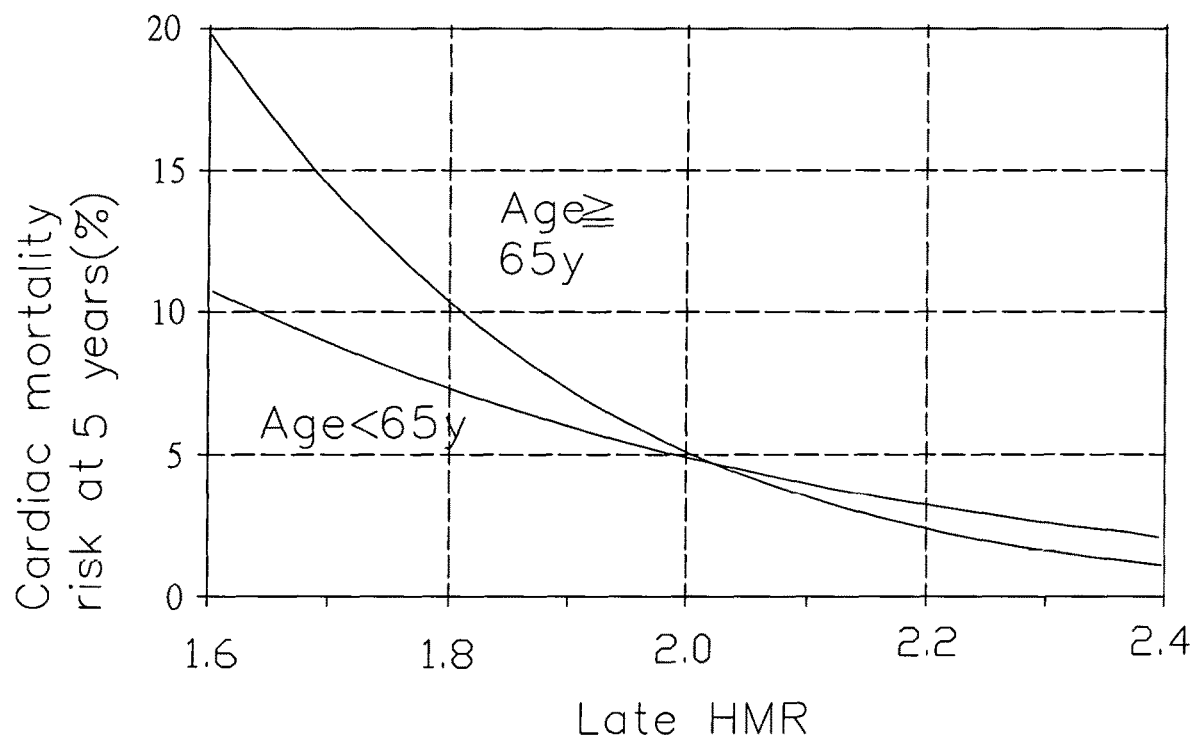
FIG. 10 is a diagram of the heart disease monitoring chart of the present invention (2).

Referring to FIG. 8, it can be seen that the present invention is effective for monitoring cardiovascular and brain functions. In practice, the application program 24 is executed in a sequence, as described below:

receiving physiological data such as heart rate and pulse pressure;

using heart rate or pulse pressure data to calculate the washout ratio;

using the washout ratio value to calculate the heart rate index value, and using the heart rate index value to calculate the early heart/mediastinum ratio or delayed heart/mediastinum ratio, monitoring heart disease risk by the early heart/mediastinum ratio or delayed heart/mediastinum ratio, monitoring whether the early heart/pseudo ratio or delayed heart/pitch ratio indicates that it is suffered from neurodegenerative diseases, and The following describes details with reference to FIG. 1 and FIG. 2, respectively. First, in the step of—receiving physiological data such as heart rate and pulse pressure, the electronic device 2 receives human physiological data such as heart rate and pulse pressure transmitted by the wearable physiological detecting device 1; in the step of—calculating the washout ration using the heart rate or pulse pressure data, it is to calculate the washout ratio value through a function of the washout ratio and the heart rate relationship, as shown in FIG. 4; the above-mentioned pulse pressure value is calculated through a washout ratio and pulse pressure relationship function, as shown in FIG. 3; in the step—calculating the heart rate index value using the washout ratio value is to calculates the heart rate index value through a function of the washout ratio and the heart rate index relationship, as shown in FIG. 5; in the step—calculating the early heart/mediastinum ratio or delayed heart/media ratio using the heart rate index value is to calculate an early heart/mediastinum ratio using the index relationship between the heart rate index and the stroke volume, as shown in FIG. 6; the heart rate index value is used to calculate the early or delayed heart/mediastinum ratio through an early or delayed heart/mediastinum ratio and heart rate index function, as shown in FIG. 7; in the step—monitoring the heart disease risk by the early heart/mediastinum ratio or delayed heart/mediastinum ratio, inputting the early or delayed heart/mediastinum ratio into a heart disease monitoring diagram, as shown in FIG. 9 and FIG. 10, to compare and monitor the risk of heart disease; in the step—monitoring neurodegenerative disease by the early or delayed heart/mediastinum ratio is to monitor the early or delayed heart/mediastinum ratio for monitoring neurodegenerative disease as shown in the FIG. 11.

Embodiment 1

When the electronic device 2 receives the pulse pressure transmitted by the wearable physiological detecting device 1 is 70 mmHg.

Figure 12:
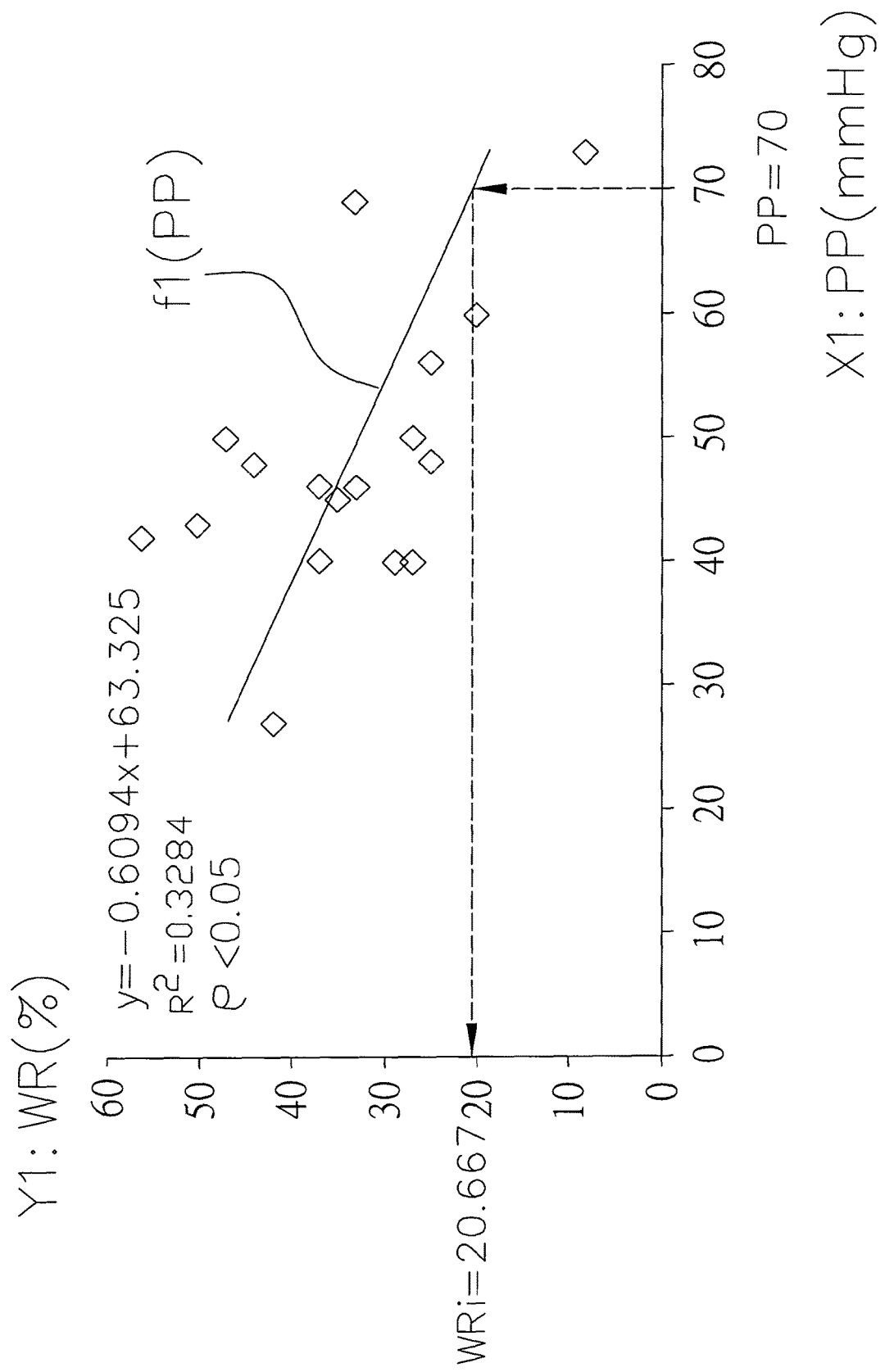
FIG. 12 is a schematic diagram of the present invention using the pulse pressure value to obtain a washout ratio value via the relationship between the washout ratio and the pulse pressure.

As shown in FIG. 12, the pulse pressure (PP) is at 70 mmHg position in horizontal axis, and draw a vertical line intersecting at the relationship curve between the washout ratio and the pulse pressure generated by Formula 1, and draw a horizontal line from the intersection to the washout ratio (WR) axis, the washout ratio of this point is recorded WRi=20.667%.

Figure 14:
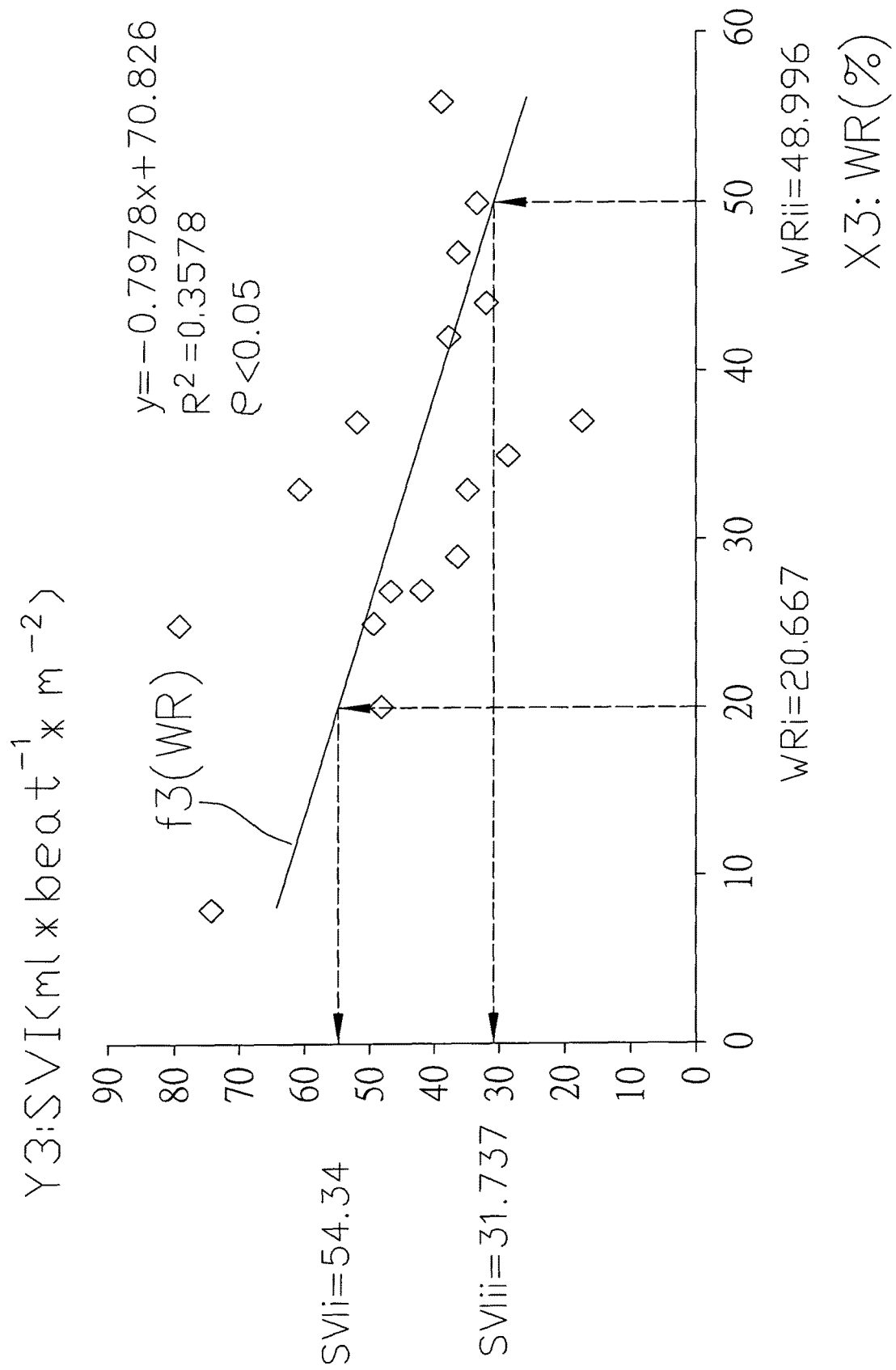
FIG. 14 is a schematic illustration of the present invention using a washout ratio value to obtain a heart rate index value via a correlation function between the washout ratio and the stroke volume index.

As shown in FIG. 14, the washout ratio (WR) is at the horizontal axis position of WRi=20.667%, and a vertical line is intersected on the relationship curve between the washout ratio and the stroke volume index generated by Formula 3, and a horizontal line is drawn from the intersection point to the stroke volume index (SVI) on the vertical axis, and the stroke volume index at this point is SVIi=54.34 ml·beat$^{-1}$·m$^{-2}$.

Figure 15:
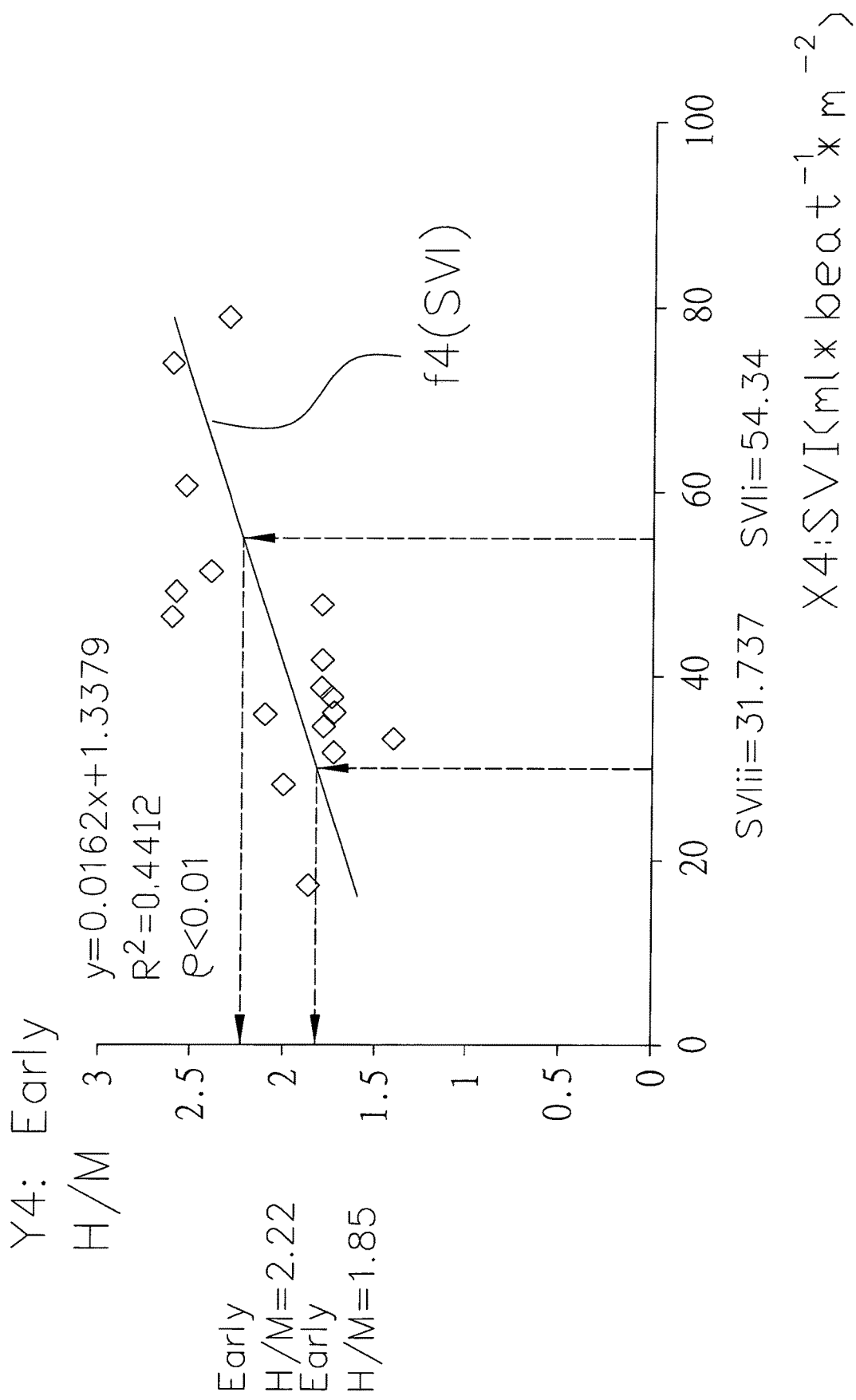
FIG. 15 is a schematic diagram of the present invention using the heart rate index value to obtain early heart/mediastinum count ratio values via the relationship between the early heart/mediastinum count ratio and the stroke volume index.
Figure 16:
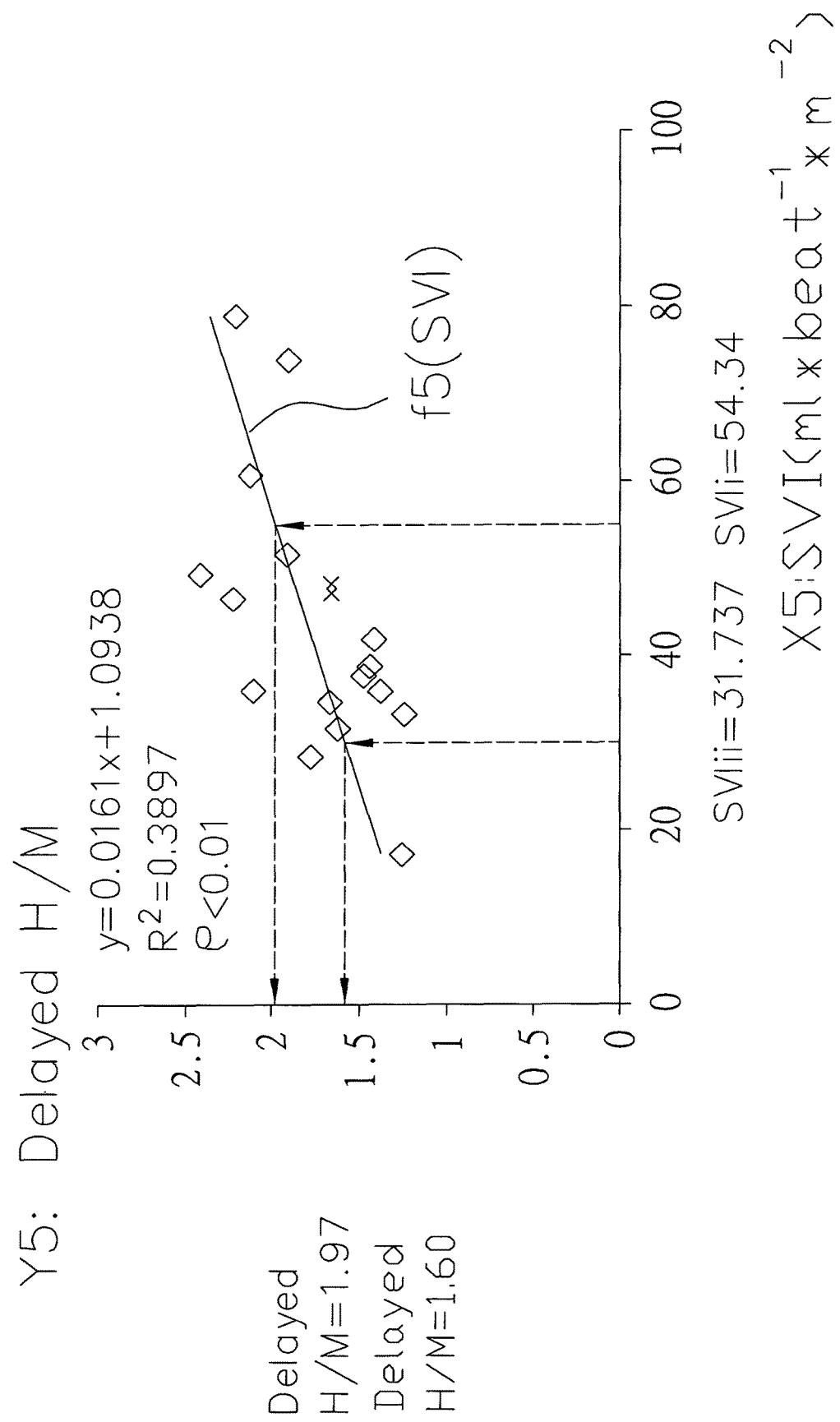
FIG. 16 is a schematic diagram of the present invention using the stroke volume index value to obtain a delayed heart/mediastinum count ratio value via the delayed heart/mediastinum count ratio and heart rate index function.

As shown in FIG. 15, the position of the stroke volume index is SVIi=54.34 ml·beat$^{-1}$·m$^{-2}$ in horizontal axis, and a vertical line is drawn to intersect on the early heart/mediastinum ratio curve generated by Formula 4, and from the intersection point a horizontal line is drawn to an early heart/mediastinum ratio on the vertical axis, the early heart/mediastinum ratio at this point is recorded as early H/Mi=2.22;

As shown in FIG. 16, the position of the stroke volume index is SVIi=54.34 ml·beat$^{-1}$·m$^{-2}$ on horizontal axis, and a vertical line is drawn to intersect on the delayed heart/mediastinum ratio curve generated by Formula 5, and from the intersection point a horizontal line is further drawn to the delayed heart/mediastinum ratio on the vertical axis, and the delayed heart/mediastinum ratio at this point is recorded as delayed H/Mi=1.97.

As shown in FIG. 9, inputting the delayed H/Mi=1.97 into the heart disease monitoring curve of delayed H/M, and both cardiac and all-cause mortality is about zero within two years.

As shown in FIG. 10, inputting the age of human and delayed H/Mi=1.97 into the heart disease monitoring curve of delayed H/M, and the cardiac mortality risk at 5 years is approximately 5%.

As shown in FIG. 11, inputting the delayed H/Mi=1.97 into the heart disease monitoring curve of delayed H/M, and the risk of Parkinson's disease and multiple system atrophy can be monitored and determined to be a medium risk, and a hospital examination is highly recommended.

Embodiment 2

When the electronic device 2 receives the heart rate transmitted by the wearable physiological detecting device 1 is 150/minute.

Figure 13:
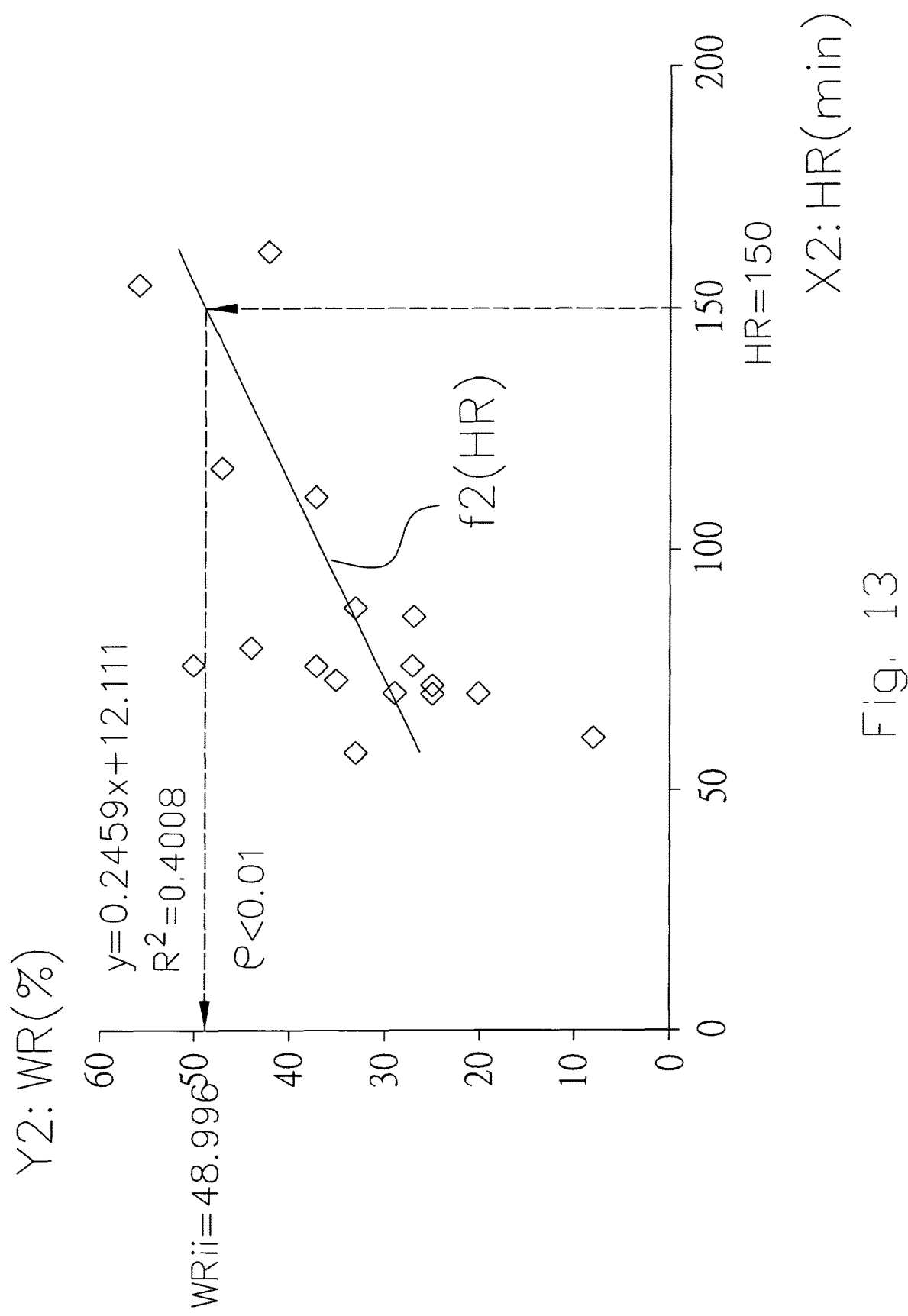
FIG. 13 is a schematic illustration of the present invention using a heart rate value to obtain a washout ratio value via the washout ratio versus heart rate function.

As shown in FIG. 13, from the position on the horizontal axis where the heart rate (HR) is 150/min, draw a vertical line to intersect the relationship curve between the washout ratio and the heart rate generated by Formula 2, and a horizontal line is drawn from the intersection point to the washout ratio (WR) on the vertical axis, and the washout ratio at this point recorded as WRii=48.996%.

As shown in FIG. 14, from the position where the washout ratio (WR) is WRii=48.996% on horizontal axis, draw a vertical line to intersect on the relationship curve between the washout ratio and the stroke volume index generated by Formula 3, and a horizontal line is drawn from the intersection point to the vertical axis of the stroke index (SVI), and the stroke index at this point is recorded as SVIii=31.737 ml·beat$^{-1}$·m$^{-2}$.

As shown in FIG. 15, the position of the stroke volume index is SVIii=31.737 ml·beat$^{-1}$·m$^{-2}$ on the horizontal axis, and a vertical line is drawn to intersect on the early heart/mediastinum ratio curve generated by Formula 4, and from the intersection point a horizontal line is further drawn to the early heart/mediastinum ratio on vertical axis, and the early heart/mediastinum ratio at this point is recorded as early H/Mi=1.85.

As shown in FIG. 16, the position of the stroke volume index is SVIii=31.737 ml·beat$^{-1}$·m$^{-2}$ on the horizontal axis, and from the intersection point a vertical line is drawn to intersect on the delayed heart/mediastinum ratio curve generated by Formula 5, and from the intersection point a horizontal line is further drawn to intersect the delayed heart/mediastinum ratio on vertical axis, and the delayed heart/mediastinum ratio of this point is recorded as delayed H/Mi=1.60.

As shown in FIG. 9, inputting the delayed H/Mi=1.60 into the heart disease monitoring curve of delayed H/M, the risk of heart disease death about 6.7% is detected and the probability of death is about 10.1%. If the related event has occurred previously, the heart failure or arrhythmia or heart disease death may occur within two years and the probability of a fatal event is 15%, which is determined as a medium risk and a hospital examination is recommended.

As shown in FIG. 10, inputting the human age and delayed H/Mi=1.60 into the heart disease monitoring curve of delayed H/M, and the cardiac mortality risk at 5 year is about 20% for the age of human being above 65 and 11% if the age of human is below 65.

As shown in FIG. 11, inputting the delayed H/Mi=1.60 into the heart disease monitoring curve of delayed H/M, the risk of developing Parkinson's disease in the first and/or second stage and progressive supranuclear palsy can be monitored and detected as a medium risk and a hospital examination is recommended.

What is claimed is:

1. A system for monitoring cardiovascular and brain functions in combination with a physiological detection device, comprising:
a wearable physiological detecting device has a host and at least one external sensing component, and the host is internally provided with a micro processing unit, a memory unit, a sensing signal receiving module and a communication control module, and the external sensing component worn on a human body is used to detect a heart rate and pulse pressure of the human body and generate a corresponding sensing signal, and the sensing signal is received by the sensing signal receiving module and converted into various physiological data, and then transmitted to the micro processing unit, wherein the memory unit stores a firmware required for the overall operation of the wearable physiological detecting device, and after executing the firmware, the micro processing unit controls the communication control module to transmit the physiological data to a paired external electronic device;
an electronic device having a computing function, comprising a central processing unit, a memory module and a communication module, wherein the communication module is capable of receiving the physiological data via a paired communication control module and transmitting the physiological data to the central processing unit, wherein the memory module is provided to store an application, having a database for storing various materials, and the application includes various calculation and derivation functions, and after the central processing unit executing the application, the physiological data is calculated and deduced through the functional formulas to generate cardiovascular and brain monitoring functions and determine the results of the analysis,
characterized in that the computing function is performed with the application built-in in the memory module to generate functions, including
a first function of the relationship between the washout ratio and the pulse pressure;
a second function of the relationship between the washout ratio and heart rate;
a third function of the relationship between the washout ratio and the stroke volume index;
a fourth function of the relationship between the early heart/mediastinum ratio and the stroke volume index;
a fifth function of the relationship between the delayed heart/media ratio and the stroke volume index.

2. The system for monitoring cardiovascular and brain functions in combination with a physiological detection device as described in claim 1, wherein the host has a switching operation module for controlling switching of different physiological detection items and actions, and the memory unit is provided with a data storage unit capable of storing the physiological data.

3. The system for monitoring cardiovascular and brain functions in combination with a physiological detection device as described in claim 1, wherein the external sensing element is disposed on the head, neck, wrist, arm, foot or other human artery part.

4. The system for monitoring cardiovascular and brain functions in combination with a physiological detection device as described in claim 1, wherein the electronic device has an operation module for performing various control actions on the central processing unit; and display modules for presentation of each operation process and calculation analysis results.

5. The system for monitoring cardiovascular and brain functions in combination with a physiological detection device as described in claim 1, wherein the electronic device is a personal computer, a notebook, tablet or a mobile phone.

6. The system for monitoring cardiovascular and brain functions in combination with a physiological detection device as described in claim 1, wherein the external sensing element is of physiological examination detected by optical sensing, electrical signal measurement or pressure sensing.

7. The system for monitoring cardiovascular and brain functions in combination with a physiological detection device as described in claim 1, wherein the transmission between the communication control module and the communication module is wireless communication.

8. A method for monitoring cardiovascular and brain functions in combination with a physiological detection device, comprising steps:

receiving a physiological data including a heart rate and a pulse pressure, wherein an electronic device is used to receive the physiological data transmitted by a wearable physiological detecting device;

calculating a washout ratio value using the heart rate or pulse pressure data by a second function of the relationship between the heart rate and the washout ratio or by a first function of the relationship between the washout ratio and the pulse pressure;

calculating a stroke volume index value with the washout ratio value by a third function of the relationship between the washout ratio and the stroke volume index;

calculating an early heart/mediastinum ratio value by a fourth function of the relationship between the early heart/mediastinum ratio and the stroke volume index, and calculating the delayed heart/mediastinum ratio by a fifth function of the relationship between the delayed heart/mediastinum ratio and the stroke volume index;

monitoring the risk of heart disease by the early heart/mediastinum ratio or delayed heart/mediastinum ratio, and inputting the early or the delayed heart/mediastinum ratio into a heart disease monitoring diagram to evaluate the risk of developing heart disease;

detecting a neurodegenerative disease by the early or delayed heart/mediastinum ratio, and inputting the early or the delayed heart/mediastinum ratio into a neurodegenerative disease monitoring diagram to evaluate the risk of developing neurodegenerative diseases.

9. The method for monitoring cardiovascular and brain functions in combination with a physiological detection device as described in claim 8, wherein the first function of the relationship between the washout ratio and the pulse pressure:

$$y=-0.6094x+63.325; R^2=0.3284; \rho<0.05$$

wherein y: washout ratio (WR); x: pulse pressure (PP); $\rho$: statistical difference value; $R^2$: coefficient of determination;

the second function of the relationship between the washout ratio and the heart rate:

$$y=0.2459x+12.111; R^2=0.4008; \rho<0.01$$

wherein y: washout ratio (WR); x: heart rate (HR); $R^2$: coefficient of determination;

the third function of the relationship between the washout ratio and the stroke volume index:

$$y=-0.7978x+70.826; R^2=0.3578; \rho<0.05$$

wherein y: stroke volume index (SVI); x: washout ratio (WR); $R^2$: coefficient of determination;

the fourth function of the relationship between the early heart/mediastinum ratio and the stroke volume index:

$$y=0.0162x+1.3379; R^2=0.4412; \rho<0.01$$

wherein y: early heart/mediastinum ratio (early H/M); x: stroke volume index (SVI); $R^2$: coefficient of determination;

the fifth function of the relationship between the delayed heart/mediastinum ratio and the stroke volume index:

$$y=0.0161x+1.0938; R^2=0.3897; \rho<0.01$$

wherein y: delayed heart/mediastinum ratio (delayed H/M); x: stroke volume index (SVI); $R^2$: coefficient of determination.

* * * * *